United States Patent
Guba et al.

(10) Patent No.: US 10,675,048 B2
(45) Date of Patent: Jun. 9, 2020

(54) SURGICAL INSTRUMENT COMPRISING PLASTIC SHAFT

(71) Applicant: Erbe Elektromedizin GmbH, Tuebingen (DE)

(72) Inventors: Joachim Guba, Weil der Stadt (DE); Lothar Mitzlaff, Lagos (PT)

(73) Assignee: Erbe Elektromedizin GmbH, Tuebingen (DE)

(*) Notice: Subject to any disclaimer, the term of this patent is extended or adjusted under 35 U.S.C. 154(b) by 355 days.

(21) Appl. No.: 14/482,665

(22) Filed: Sep. 10, 2014

(65) Prior Publication Data

US 2015/0073462 A1  Mar. 12, 2015

(30) Foreign Application Priority Data

Sep. 10, 2013 (EP) ..................................... 13183642
Sep. 12, 2013 (EP) ..................................... 13184193

(51) Int. Cl.
*A61B 17/295* (2006.01)
*A61B 18/14* (2006.01)
(Continued)

(52) U.S. Cl.
CPC ........ *A61B 17/295* (2013.01); *A61B 18/1445* (2013.01); *A61B 2017/2936* (2013.01);
(Continued)

(58) Field of Classification Search
CPC .......... A61B 2017/2938; A61B 17/295; A61B 18/1442; A61B 18/1445; A61B 18/1447;
(Continued)

(56) References Cited

U.S. PATENT DOCUMENTS 5,423,848 A * 6/1995 Washizuka ............. A61B 17/34
604/164.11
5,458,598 A * 10/1995 Feinberg ............ A61B 18/1445
606/205
(Continued)

FOREIGN PATENT DOCUMENTS

CN 102791218 A 6/2015
EP 2294998 A1 3/2011
(Continued)

OTHER PUBLICATIONS

Notice of Preliminary Rejection for corresponding Korean Application No. 2014-0117751, dated Oct. 21, 2015, 12 pages.
(Continued)

*Primary Examiner* — Ronald Hupczey, Jr.
(74) *Attorney, Agent, or Firm* — Fitch, Even, Tabin & Flannery LLP

(57) ABSTRACT

In the case of an electrosurgical instrument, provision is made for a tool (16), for the operation of which at least one, preferably two pull/thrust elements (39, 40) and a sliding element (56) are required. The sliding element (56) is held between a pull/thrust element (39) and a thrust bearing, wherein the thrust bearing can be formed by means of a further pull/thrust element (40). This arrangement utilizes the fact that the sliding element must only be activated, when the pull/thrust element is tensioned tightly. This concept of guiding the sliding element at the pull/thrust element provides for the simple design of instruments comprising long shafts, wherein separate measures for laterally reinforcing the sliding elements do not need to be taken.

18 Claims, 3 Drawing Sheets

(51) Int. Cl.
*A61B 17/29* (2006.01)
*A61B 18/00* (2006.01)

(52) U.S. Cl.
CPC .............. *A61B 2017/2938* (2013.01); *A61B 2017/2939* (2013.01); *A61B 2018/0063* (2013.01); *A61B 2018/1455* (2013.01)

(58) Field of Classification Search
CPC .... A61B 2018/1452; A61B 2018/1455; A61B 17/285; A61B 2017/2932; A61B 2017/2933; A61B 2017/294
See application file for complete search history.

(56) References Cited

U.S. PATENT DOCUMENTS

| | | | | |
|---|---|---|---|---|
| 5,665,100 | A | * | 9/1997 | Yoon ................... A61B 10/06 606/139 |
| 5,800,449 | A | | 9/1998 | Wales |
| 5,827,279 | A | * | 10/1998 | Hughett ............ A61B 18/1447 606/45 |
| 6,554,829 | B2 | | 4/2003 | Schulze et al. |
| 2003/0114851 | A1 | * | 6/2003 | Truckai .............. A61B 18/1445 606/51 |
| 2005/0124986 | A1 | | 6/2005 | Brounstein et al. |
| 2011/0034918 | A1 | | 2/2011 | Reschke |
| 2011/0196419 | A1 | | 8/2011 | Cooper |
| 2011/0245825 | A1 | | 10/2011 | Mitzlaff et al. |
| 2011/0251612 | A1 | * | 10/2011 | Faller ................. A61B 18/1445 606/52 |
| 2012/0035623 | A1 | | 2/2012 | Bagaoisan et al. |
| 2013/0066303 | A1 | | 3/2013 | Hart |

FOREIGN PATENT DOCUMENTS

| | | |
|---|---|---|
| EP | 2371316 A1 | 10/2011 |
| EP | 2574299 A2 | 3/2013 |
| JP | 2002330973 A | 11/2002 |
| JP | 2007513695 A | 5/2007 |
| JP | 2010057934 A | 3/2010 |
| JP | 2012515020 A | 7/2012 |
| WO | 2012151493 A2 | 11/2012 |

OTHER PUBLICATIONS

Russian office action in corresponding Russian application No. 2014136540, dated Nov. 16, 2015, 6 pages.
Japanese office action in corresponding Japanese application No. 2014-182191, dated Nov. 13, 2015, 6 pages.
Japanese search report in corresponding Japanese application No. 2014-182191, dated Nov. 12, 2014, 29 pages.
First office action and search report in corresponding Chinese application No. 201410457150.5, dated Apr. 16, 2016, 20 pages.
Decision of Refusal in corresponding Japanese application No. 2014-182191, dated Aug. 16, 2016, 4 pages.
Office action in corresponding European application No. 13 184193, dated May 24, 2016, 6 pages.
European Search Report for corresponding European Application No. 13184193.4, dated Jan. 8, 2014, 7 pages.
Office Action dated Nov. 29, 2018 for corresponding Indian Application No. 791/KOL/2014 (5 pgs.).

* cited by examiner

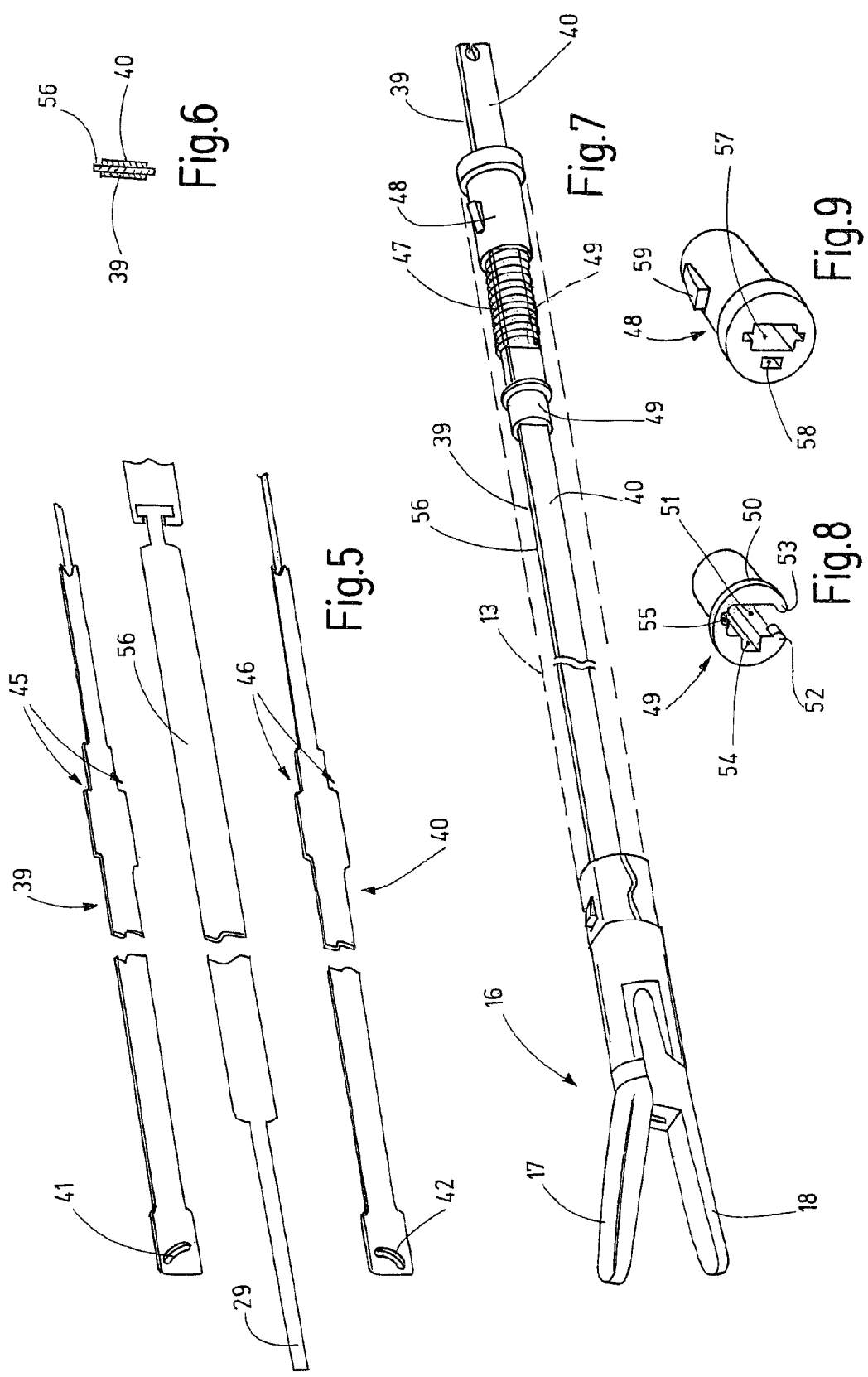

SURGICAL INSTRUMENT COMPRISING PLASTIC SHAFT

RELATED APPLICATION(S)

This application claims the benefit of European Patent Application No. EP13183642.1 filed Sep. 10, 2013 and European Patent Application No. EP13184193.4 filed Sep. 12, 2013, the contents of each of which are incorporated herein by reference as if fully rewritten herein.

TECHNICAL FIELD

The invention relates to a surgical instrument, in particular an electrosurgical instrument, comprising an elongated shaft, through which pull/thrust and sliding elements extend for operating a tool, which is arranged at the distal end of the shaft.

BACKGROUND

The term "distal" hereinbelow will always describe the part of the instrument or component, which is located at a distance from the user, the term "proximal" will always describe the part of the instrument or component, which is located closer and which points towards the user.

EP 2 371 316 A1 discloses an electrosurgical instrument for coagulating, sealing and severing biological tissue, such as blood vessels, for example. The instrument encompasses a tool comprising a movable branch, which can be moved towards another branch, so as to seize and clamp the tissue as well as to supply it with current. The tool also includes a blade, which can be moved linearly, so as to sever the sealed tissue. The tool is arranged at the distal end of an elongated shaft, the proximal end of which is held at a housing. The housing encloses an operating drive for the tool and encompasses a handle as well as an operating lever. The operating drive transfers the movement of the operating lever to the tool, so as to close the branches and so as to push the blade forwards. The movement converted by the operating drive is transferred to the tool by means of pull/thrust and sliding elements, which extend through the shaft.

So that the blade executes a straight incision reliably, it must be capable of being operated safely by means of the sliding element, which extends through the shaft. For this purpose, the sliding element must be guided in the shaft, so that it does not evade laterally in response to a translatory motion. However, guidance requires play, so that the sliding element can be operated smoothly. If the sliding element evades the translatory motion laterally, increased friction and inaccurate blade movement can occur in the guidance.

SUMMARY

It is the object of the invention to create a surgical instrument, which operates reliably independent from the shaft length, comprising at least one movable branch and comprising at least one linearly movable blade.

The surgical instrument according to the invention encompasses a tool comprising two branches, at least one of which is supported so as to be pivotably movable. Preferably, the branches are provided with electrode units, which encompass electrically conductive tissue contact surfaces, which serve as electrodes and between which biological tissue, in particular blood vessels, are to be seized and compressed. The tissue contact surfaces of the electrode units are connected or can be connected to an electrical source, for example a HF generator. Current can be supplied to them via a switch, which is preferably arranged at the housing of the instrument, so as to coagulate or to seal biological tissue, which is seized therebetween.

The tool further includes a blade, which can be moved in a sliding manner in distal direction in a suitable blade guide groove, which is provided in the branches, so as to sever tissue, which is seized between the electrode units of the branches.

The tool is held in an elongated shaft, which is embodied so as to be straight and which extends away from the housing. In its longitudinal direction, the shaft encompasses an opening and thus surrounds a channel, through which at least one element extends, so as to provide at least one of the branches with a movement for closing or opening, respectively. This element, a pull/thrust element, is subjected to shearing stresses in response to closing and is subjected to tensile stresses in response to opening a branch. If both branches are movable, up to two pull/thrust elements can extend through the channel of the shaft, so as to move the branches towards one another when the pull/thrust elements are moved so as to be pulled. The opening, which extends in the interior of the shaft, the channel, can be formed variably, for example cylindrical, conical or in a different way.

The blade is operated by means of a sliding element. The latter is arranged between at least one pull/thrust element and a thrust bearing and extends through the shaft parallel to the pull/thrust element. The thrust bearing can be a surface of the shaft or, if present, a second pull/thrust element. This arrangement utilizes the fact that the blade can only be moved in a sliding manner in distal direction, if the two branches fixedly press against one another and, if applicable, clamp tissue, preferably coagulated tissue, between the electrode units. In this state, the two pull/thrust elements are stretched tightly, so as to provide the branch or the branches with the necessary torque for closing. In this state, the sliding element can be guided between the pull/thrust elements without being bent. This makes it possible to embody the sliding element as a flat, strip-shaped element, for example as a metal band, which runs substantially centrically through the shaft, for example, and which is supported on both flat sides by the stretched pull/thrust elements. The latter are subjected to tensile stresses and can thus accurately guide the sliding element with only small play and low friction.

The pull/thrust elements can be embodied in a wire or strip-shaped manner. Preferably, they consist of metal. The sliding element also preferably consists of metal. It can be embodied integrally with the blade.

Preferably, the blade is guided so as to be linearly movable in a base part. The base part can furthermore serve the purpose of accommodating one or both branches in a pivotably movable manner. It is arranged at one end of the shaft. The base part and the shaft can be embodied integrally, without a seam. Preferably, a pipe end sleeve, which performs a parallel insertion of sliding element and pull/thrust element(s), is arranged at the opposite proximal end of the shaft. The sliding and pull elements are thus accurately guided at both ends of the shaft. The pipe end sleeve can be connected integrally to the shaft without a seam.

Further details of advantageous embodiments and details of the invention are the subject matter of the description, of the drawings or of the claims.

BRIEF DESCRIPTION OF THE DRAWINGS

FIG. 5 shows pull/thrust and sliding elements for the tool according to FIG. 2 in perspective exploded illustration, FIG. 6 shows the pull/thrust and sliding elements according to FIG. 5 in cross sectional view and in installed position, FIG. 7 shows the tool comprising the shaft and pull/thrust and sliding elements in a perspective schematic diagram, FIG. 8 shows a cable guide sleeve for the pull/thrust elements according to FIG. 7 in perspective illustration and FIG. 9 shows a pipe end sleeve for the arrangement according to FIG. 7 in perspective illustration.

DETAILED DESCRIPTION

Figure 1:
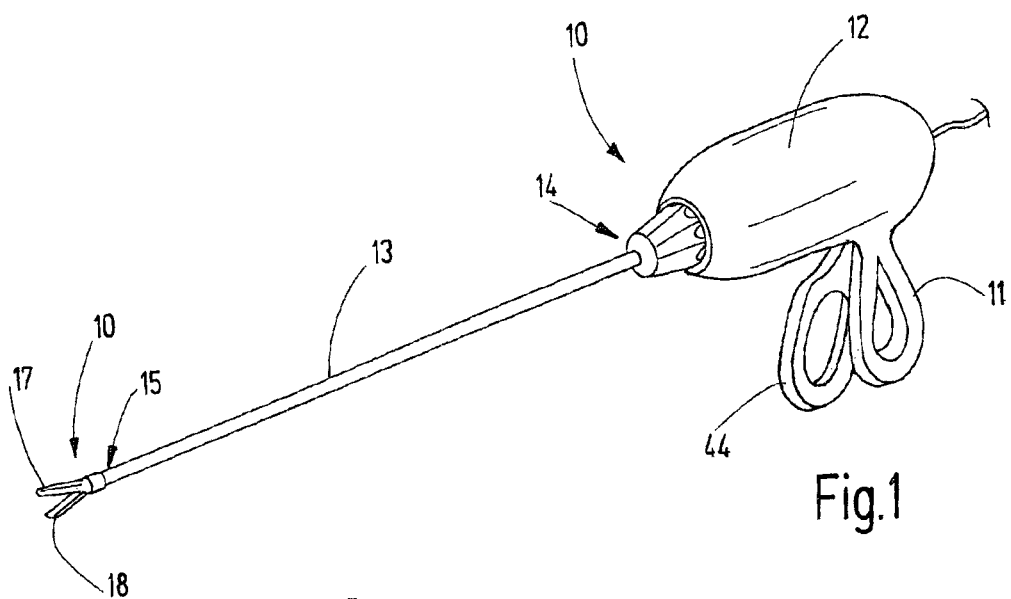
FIG. 1 shows the instrument according to the invention in a perspective schematic diagram.

FIG. 1 illustrates a surgical instrument 10, which encompasses a housing 12, which is provided with a handle 11. A shaft 13, the proximal end 14 of which is held at the housing 12. The distal end 15 of the shaft 13 supports a tool 16 for acting on biological material, for example for clamping, coagulating and fusing, as well as for the subsequent severing of tissue, for example blood vessels.

Figure 2:
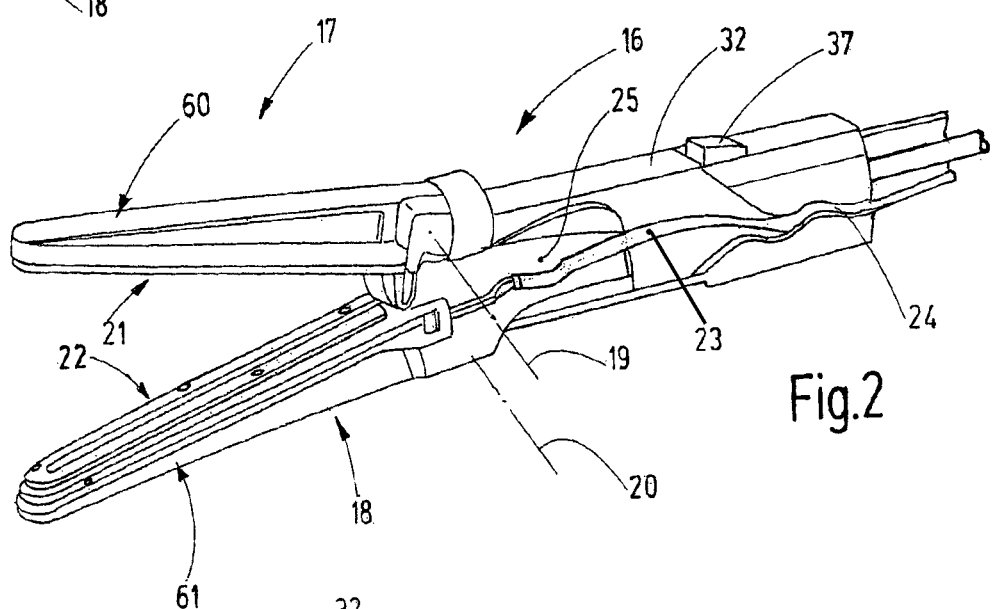
FIG. 2 shows the tool of the instrument according to FIG. 1 in perspective illustration.
Figure 3:
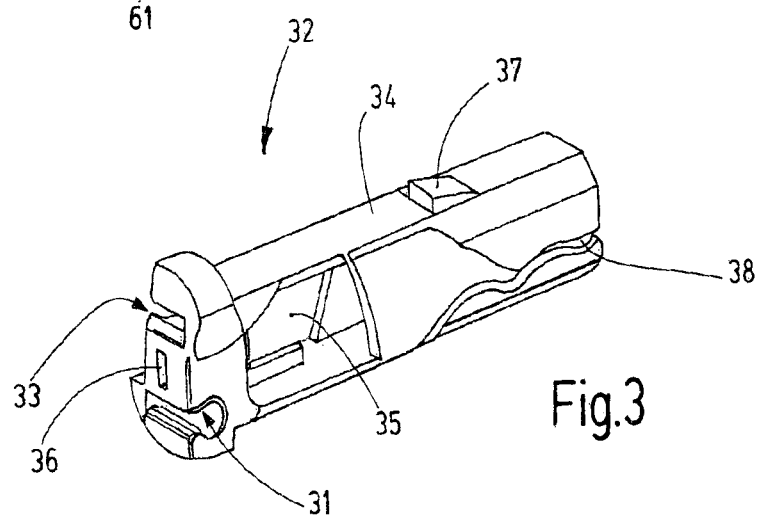
FIG. 3 shows a base part, which belongs to the tool according to FIG. 2, in perspective illustration.
Figure 4:
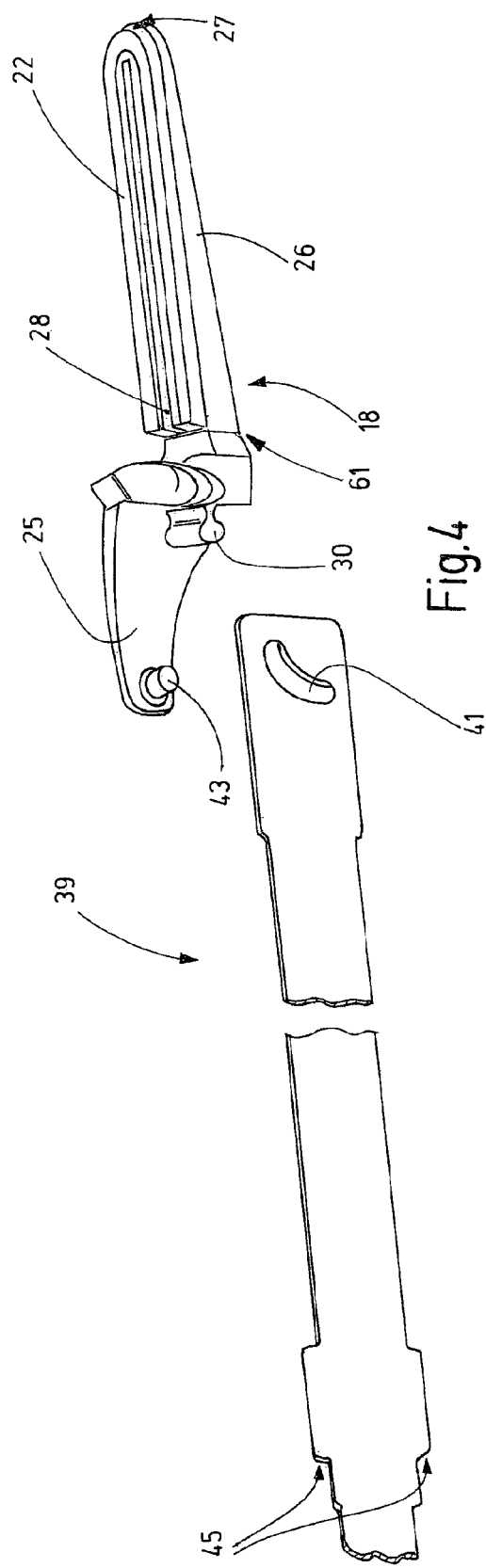
FIG. 4 shows a branch and its corresponding pull/thrust element in perspective illustration.

The tool 16 is illustrated separately in FIG. 2. It encompasses a first branch 17 and a second branch 18, at least one of which, in the exemplary embodiment at hand both branches 17, 18, are supported so as to be pivotably movable about hinge axes 19, 20. Each branch 17, 18 consists of a branch support 60, 61 and the electrode units 21, 22, which are fixed thereto. The branch supports 60, 61 thereby serve to transfer the mechanical forces and to store the branches 17, 18. The branches 17, 18 encompass electrode units 21, 22, to which electrical energy can be applied via electrical lines. For this purpose, the line 23, which is connected to the electrode unit 22, can be seen in FIG. 2. The core of the line 23 is connected to a sheet metal part of the electrode unit 22, which also forms the tissue contact surface. The line 23 is insulated in the further course and is held a corrugated channel 24, which extends through an operating part 25 of the branch support 61 of the branch 18. As can be seen in FIG. 4, the branch support 61 of the branch 18 comprises a tool part 26, which is located opposite the operating part 25 and which supports the electrode unit 22. Provision is made in the center of the electrode unit 22 for a channel, which is insulated on both sides, or for a blade guide groove 28, which serves to accommodate a blade 29 (FIG. 5). At its distal front side, at right angles to its direction of motion, the blade 29 encompasses a cutting edge.

Between the operating part 25 and the tool part 26, the branch support 61 of the branch 18 is provided with a bearing pin 30, which can be inserted into a bearing sleeve 31 of a base part 32. Parallel to the bearing sleeve 31, the base part 32, which preferably consists of plastic, encompasses a further bearing sleeve 33 for the first branch 17, which is designed similar to the above-described second branch 18 or as common part thereto. The electrode unit 21 of the branch 17 is accordingly also connected to an electrical source via a corresponding line.

The base part 32 encompasses an appendage 34, which can be inserted into the shaft 13 and which can be locked thereto and which surrounds a central window 35. Between the bearing sleeves 31, 33, it transitions into a slit 36 for guiding the blade 29.

One or a plurality of lugs 37 for locking to the shaft 13 are embodied at the appendage 34. Corrugated grooves 38 for fixing and tension-protecting the line 23, are also embodied at the appendage 34 at both shoulders.

As can be seen from FIG. 5, pull/thrust elements 39, 40 serve to operate the branches 17, 18, that is, to pivot them. They preferably consist of narrow sheet metal strips comprising a distally arranged cam guide 41, 42 for accommodating an operating pin 43 in each case, as it can be seen from FIG. 4 at the branch support 61 of the branch 18. A similar operating pin is provided at the branch 17.

As can be seen in FIG. 7, the two pull/thrust elements 39, 40 extend through the entire shaft 13 into the housing 12. A force transfer means for transferring an operating movement, which is exerted on an operating lever 44, onto the pull/thrust elements 39, 40, is located in said housing.

In the vicinity of its proximal end, the pull/thrust elements 39, 40 encompass recesses 45, 46, which serve to support a compression spring 47. At its other end, the compression spring 47 is supported on a pipe end sleeve 48, as it can be seen from FIG. 9.

A cable guide sleeve 49 according to FIG. 8 is also located on the pull/thrust elements 39, 40 within the shaft 13. The cable guide sleeve 49 is embodied as plastic injection molded part, for example. It is arranged at least on one side of the recesses 45, 46 or on both sides, as in the position illustrated in FIG. 7, for example, and additionally within the compression spring 47. The primary function of the cable guide sleeve 49 is to hold one or a plurality of electrical lines, such as the line 23, for example, in a defined position and to thus prevent that the lines are jammed in the compression spring 47.

The cable guide sleeve 49 illustrated in FIG. 7 on the right by means of a dashed reference line forms a stop for the compression spring 47. For this purpose, it encompasses a radial flange or collar 50. The cable guide sleeve 49 encompasses a central channel 51, which has a substantially rectangular cross section, which is slotted towards the bottom, so that the cable guide sleeve 49 can be slid over the pull/thrust elements 39, 40. At the lower edge of the channel 51, the collar 50 encompasses lugs 52, 53 for holding the cable guide sleeve 49 on the pull/thrust elements 39, 40. Laterally and towards the top, the channel 51 is widened by means of groove-like depressions 54, 55. Electrical lines or cables can be accommodated in the depression 54. The depression 55 serves to guide a sliding element 56, which will be explained below. It is not required for the cable guide sleeves 49 to be embodied geometrically identical. It is important that the cable guide sleeves 49 encompass the features described above.

The sliding element 56 belongs to the blade 29. It is embodied integrally therewith, for example, in the form of a flat sheet metal strip comprising an even thickness. The height (to be measured vertically in FIG. 5) of the sliding element 56 is preferably larger than the height of the blade 29. In addition, the height of the sliding element 56 is preferably slightly larger than the height of the pull/thrust elements 39, 40. The ratios are illustrated in FIG. 6, which reflects a section at a location, which is located in the shaft 13. As can be seen, the sliding element 56 projects beyond the pull/thrust elements 39, 40 on the top and/or on the bottom. The upper part of the sliding element 56 can be guided in the depression 55.

The pipe end sleeve 48 also encompasses a channel 57, which is adapted to the cross section, which is illustrated in FIG. 6 as a whole. Provision can be made for a passage 58 for electrical lines next to and parallel to said channel 57. In addition, the pipe end sleeve 48 can be provided with a lug 59 for fastening to the shaft 13.

The instrument 10, which was described in this respect, works as follows:

In the non-operated state, the branches 17, 18 are spread away from one another and the cutting edge of the blade 29 is located within the base part 32. The compression spring 47 pushes the pull/thrust elements 39, 40 in distal direction, whereby the branches 17, 18 remain spread.

In the event that the user now operates the operating lever 44, a drive, which is arranged in the housing 12, transfers this operating movement into a pull movement, which is transferred to the proximal ends of the pull/thrust elements 39, 40. This pull movement in proximal direction closes the branches 17, 18 against the force of the compression spring 47. The branches 17, 18 seize the biological tissue located between them and hold it so as to be clamped tightly. The tissue can be supplied with a current and can be coagulated by means of a switch, which is not illustrated in detail and by activating a connected generator via the electrode units 21, 22.

In the event that the coagulated tissue is to now be severed, for example, the mechanism, which is arranged in the housing 12, moves the sliding element 56 in distal direction. The sliding element 56 can encompass a length of several 100 mm, for example 265 mm, wherein it encompasses a smaller thickness of only between 0.2 and 0.3 mm, for example. It is held between the tensioned pull/thrust elements 39, 40 and can thus not buckle laterally. By means of cutting edges, which are provided at the front surface, said sliding element thus pushes the blade 29, which, in turn, is guided securely in the blade guide groove 28, through denatured tissue with the required force and severs it safely by means of a clean cut.

In the case of the electrosurgical instrument 10, provision is made for a tool 16, for the operation of which at least one, preferably two pull/thrust elements 39, 40 and a sliding element 56 are required. The sliding element 56 is held between a pull/thrust element 39 and a thrust bearing, wherein the thrust bearing can be formed by means of a further pull/thrust element 40. This arrangement utilizes the fact that the sliding element 56 must only be activated, when the pull/thrust element 39 (40) is tensioned tightly. This concept of guiding the sliding element 56 at the pull/thrust element(s) 39 (40) provides for the simple design of instruments comprising long shafts, wherein separate measures for laterally reinforcing the sliding element do not need to be taken. A plastic pipe can be used to embody the shaft 13. The opening, the channel, which extends in longitudinal direction of the pie, can be formed variably, for example cylindrical, conical or in a different way.

LIST OF REFERENCE NUMERALS 10 instrument
11 handle
12 housing
13 shaft
14 proximal end of the shaft 13
15 distal end of the shaft 13
16 tool
17 first branch
18 second branch
19 hinge axis of the first branch 17
20 hinge axis of the second branch 18
21 electrode unit of the first branch 17
22 electrode unit of the second branch 18
23 line
24 corrugated channel
25 operating part
26 tool part
28 blade guide groove
29 blade
30 bearing pin
31 bearing sleeve for the second branch 18
32 base part
33 bearing sleeve for the first branch 17
34 appendage
35 window
36 slit
37 lug
38 groove
39, 40 pull/thrust element
41, 42 cam guide
43 operating pin
44 operating lever
45, 46 recesses
47 compression spring
48 pipe end sleeve
49 cable guide sleeve
50 collar
51 channel
52, 53 lugs
54, 55 depressions
56 sliding element
57 channel
58 passage
59 lug
60, 61 branch support

What is claimed is:

1. A surgical instrument (10), comprising:
   a tool (16) comprising:
      a blade (29), which can be moved in a sliding manner,
      a first and a second branch (17, 18), at least the first branch (17) of which is supported so as to be pivotably movable,
      an operating lever operably connected to at least the first branch for pivotably moving at least the first branch;
   an elongated shaft (13), which is embodied so as to be straight and which includes a distal end (15), at which the tool (16) is held,
   wherein the first branch is mounted at a distal end of the elongated shaft so as to be pivotably movable about a hinge axis that is stationary relative to the elongated shaft;
   a first pull/thrust element (39, 40) connected to the operating lever and configured to move longitudinally in a proximal direction within the stationary shaft to actuate at least the first branch (17) when the operating lever is actuated so as to move the branches (17, 18) from an open position to a closed position, wherein the first pull/thrust element (39, 40) is a wire or a strip-shaped element that extends longitudinally through the shaft (13),
   a sliding element (56) separately movable from the first wire or strip-shaped pull/thrust element and that extends through the shaft (13) between the first wire or strip-shaped pull/thrust element (39, or 40) and an abutment separate from the sliding element and the first wire or strip-shaped pull/thrust element and extending longitudinally along the shaft's length, and
   further configured wherein the first wire or strip-shaped pull/thrust element, when in tension in response to operation of the operating lever (44) connected to actuate the first wire or strip-shaped pull/thrust element, and the abutment engage and support sides of the sliding element along a substantial portion of the shaft's length to prevent bending of the sliding element when the sliding element is pushed through the shaft to slide the blade.

2. The instrument according to claim 1, wherein abutment is formed by the shaft (13).

3. The instrument according to claim 1 wherein both branches (17, 18) are arranged so as to be pivotably movable.

4. The instrument according to claim 3, further comprising a second pull/thrust element (39, 40) configured to engage one of the branches (17, 18) to which the first wire or strip-shaped pull/thrust element is not assigned.

5. The instrument according to claim 4, wherein the abutment is formed by the second pull/thrust element (40).

6. The instrument according to claim 5, wherein the second pull/thrust element (40) is a wire or a strip-shaped element.

7. The instrument according to claim 5, wherein the sliding element (56) is held between the pull/thrust elements (39, 40) so as to be rest against them, wherein the pull/thrust elements (39, 40) rest against flat sides of the sliding element (56).

8. The instrument according to claim 1 wherein the shaft (13) is made from plastic.

9. The instrument according to claim 1 wherein the shaft (13) encompasses a conical channel, which extends in longitudinal direction.

10. The instrument according to claim 1 wherein the sliding element (56) is embodied integrally with the blade (29).

11. The instrument according to claim 1 wherein the blade (29) is guided so as to be linearly movable in a base part (32).

12. The instrument according to claim 11, wherein the base part (32) is made from plastic.

13. The instrument according to claim 11 wherein the branches (17, 18) are supported on the base part (32).

14. The instrument according to claim 11 wherein the base part (32) is locked in place with the shaft (13).

15. The instrument according to claim 1, wherein the first wire or strip-shaped pull/thrust element includes a cam guide (41) that engages directly with an operating pin (43) of the first branch for pivoting the first branch about the hinge axis when the first wire or strip-shaped pull/thrust element is shifted longitudinally in the proximal direction.

16. A method of operating a surgical instrument (10) comprising a tool (16) that comprises a blade and first and second branches (17, 18), the method comprising:
  moving the blade (29) in a sliding manner;
  pivotally moving at least the first branch (17) of the first and second branches (17, 18);
  moving a first pull/thrust element (39, 40) in the form of a wire or a strip-shaped element that extends through an elongated shaft of the tool and that is assigned to one of the branches (17, 18) proximally relative to the stationary shaft so as to move the branches (17, 18) from an open position to a closed position by pivoting at least the first branch about a hinge axis that is stationary with respect to the elongated shaft, wherein moving the first wire or strip-shaped pull/thrust element proximally includes operating an operating lever (44) connected to the first wire or strip-shaped pull/thrust element to put the first wire or strip-shaped pull/thrust element in tension:
  holding a sliding element (56) separately movable from the first wire or strip-shaped pull/thrust element and that extends through the shaft (13), between the first wire or strip-shaped pull/thrust element (39, or 40) and an abutment extending longitudinally along the shaft's length wherein the first wire or strip-shaped pull/thrust element and the abutment are separate from the sliding element and the first wire or strip-shaped pull/thrust element when in tension and the abutment engage and support opposing sides of the sliding element along a substantial portion of the shaft's length to prevent bending of the sliding element when the sliding element is pushed through the shaft to slide the blade.

17. The method according to claim 16 wherein the holding the sliding element (56) comprises holding the sliding element between the first wire or strip-shaped pull/thrust element (39) and a second pull/thrust element (40) so as to be rest against them, wherein the first and second pull/thrust elements (39, 40) rest against flat sides of the sliding element (56).

18. The method according to claim 16 wherein the moving the blade comprises sliding the sliding element (56) to move the blade.

* * * * *